(12) United States Patent
Farin et al.

(10) Patent No.: US 6,391,027 B1
(45) Date of Patent: May 21, 2002

(54) GAS-AIDED, AXIALLY DISPLACEABLE SURGICAL ELECTRODE

(75) Inventors: Günter Farin, Tübingen; Klaus Fischer, Nagold; Volker Bartel, Gomaringen, all of (DE)

(73) Assignee: Erbe Elektromedizin GmbH (DE)

( * ) Notice: Subject to any disclaimer, the term of this patent is extended or adjusted under 35 U.S.C. 154(b) by 0 days.

(21) Appl. No.: 09/214,329
(22) PCT Filed: Jul. 4, 1997
(86) PCT No.: PCT/EP97/03552
  § 371 Date: Aug. 9, 1999
  § 102(e) Date: Aug. 9, 1999
(87) PCT Pub. No.: WO98/01075
  PCT Pub. Date: Jan. 15, 1998

(30) Foreign Application Priority Data

Jul. 4, 1996 (DE) .......................................... 196 26 976

(51) Int. Cl.⁷ .............................................. A61B 18/18
(52) U.S. Cl. ............................... 606/45; 606/34; 606/47
(58) Field of Search ............................ 606/41–50, 32, 606/34, 38

(56) References Cited

U.S. PATENT DOCUMENTS

| | | | | |
|---|---|---|---|---|
| 5,496,314 A | * | 3/1996 | Eggers | 606/41 |
| 5,667,488 A | * | 9/1997 | Lundquist et al. | 604/22 |
| 5,693,044 A | * | 12/1997 | Cosmescu | 606/42 |

\* cited by examiner

Primary Examiner—Linda C. M. Dvorak
Assistant Examiner—David Ruddy
(74) Attorney, Agent, or Firm—St. Onge Steward Johnston & Reens LLC

(57) ABSTRACT

The invention concerns a surgical instrument preferably for high-frequency surgery, which is designed for simple operation. For this purpose, by means of an operating device consisting of a movable handle and a grip handle, the housing 8 of the instruments of the electrode 5 moves longitudinally, through the motion of the thumb, so that the electrode 6 can be brought into working position or an APC mode can be selected. Through spring force, for instance, upon activation of a catch button or by setting aside the instrument, the electrode can automatically be retracted into the housing 8 or the housing 8 can be brought to a position surrounding the electrode 5.

14 Claims, 7 Drawing Sheets

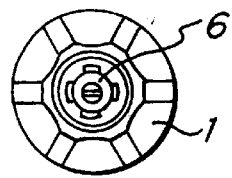
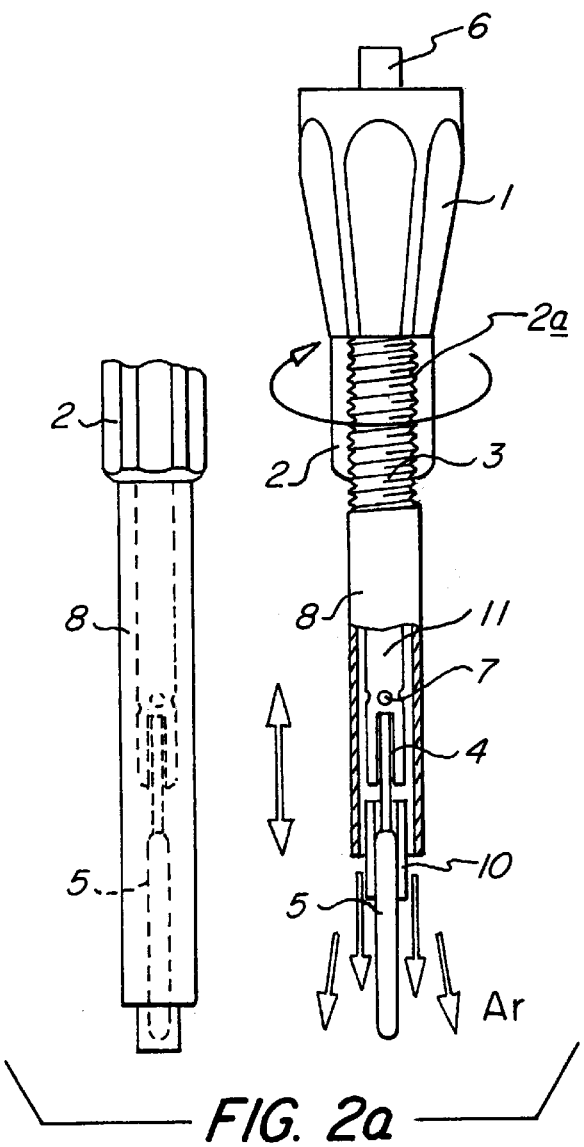
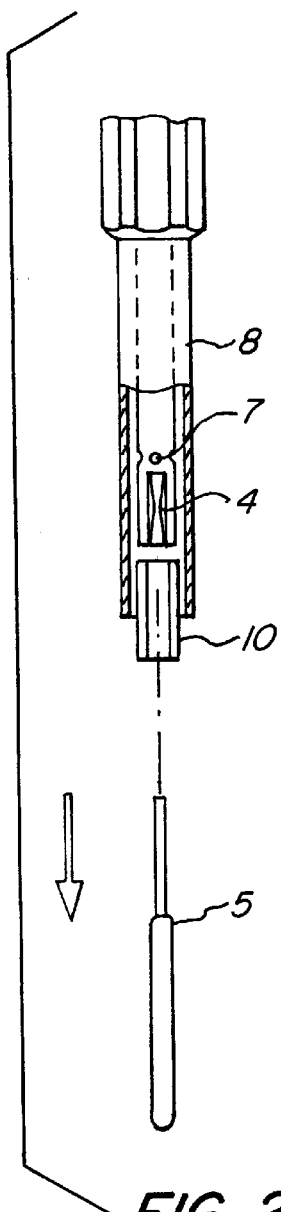
FIG. 2a
FIG. 2b

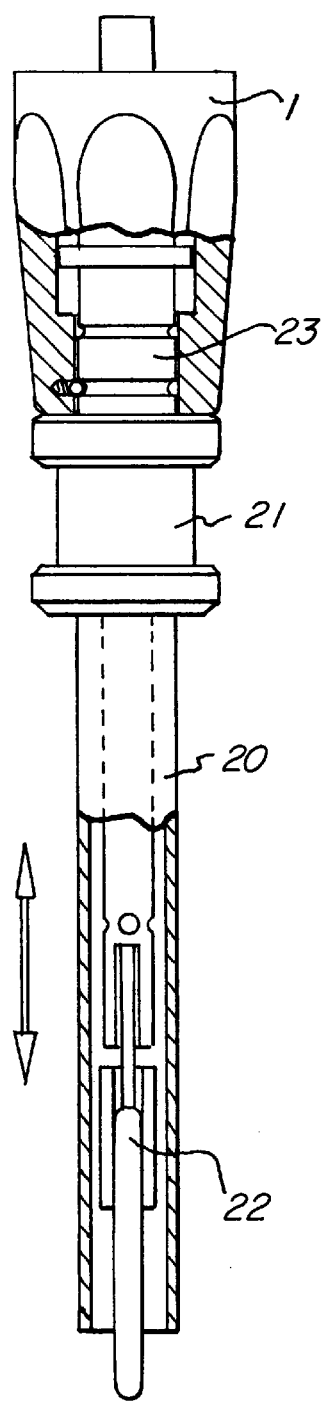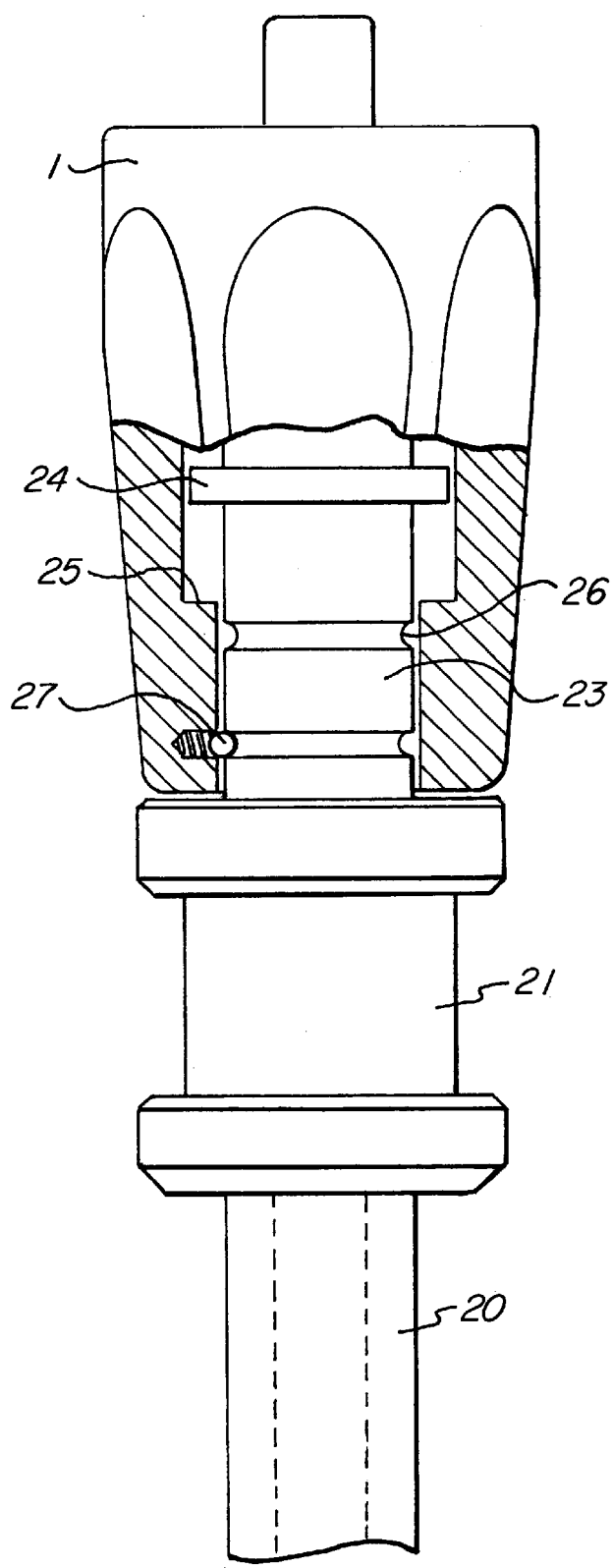
FIG. 7a
FIG. 7b

GAS-AIDED, AXIALLY DISPLACEABLE SURGICAL ELECTRODE

FIELD OF THE INVENTION

The invention concerns a surgical instrument preferably for high frequency surgery wherein an electrode can be covered by an axially movable housing.

BACKGROUND OF THE INVENTION

Surgical instruments for high-frequency surgery have been well known for some time in various models. U.S. Pat. No. 5,007,008 describes an electric surgical instrument that is equipped on its distal end with a monopolar or bipolar coagulation electrode, from which a needle electrode suitable for cutting can be extended as needed. The instrument has the disadvantage that the operator must move the needle electrode manually out of the instrument while simultaneously activating the cutting mode of the high-frequency surgical instrument being used, and thus the handling in general is more difficult.

Patent application DE 195 37 897.0 presents a multifunction element which incorporates various individually guidable and activatable applicators, cutting and coagulation electrodes, a laser and an ultrasound wave and the like, in a revolver arrangement within the apparatus. An individual applicator is moved to the distal end of the instrument into working position by way of a piezoelectric, electromagnetic, and/or hydraulic activator. The activator can also be directly addressed by way of a speech recognition module. Such a multivalent device, however, is costly.

Therefore, this invention aims to propose a simple surgical instrument, preferably for high-frequency surgery, that is economical to produce and simple to operate.

SUMMARY OF THE INVENTION

The basic idea of the invention is to provide a surgical instrument, preferably for high-frequency surgery, the various functions of which can be controlled with one hand.

For this purpose the instrument includes a handling device, a housing, connections for high-voltage current and gas, and an exchangeable electrode on its distal end.

Control of the instrument—that is, the movement of the electrode in and out of the housing, or the retracting and extending of the housing, and the change from cutting to APC (argon-plasma-coagulation) mode—occurs through the longitudinally mounted handling device, which consists basically of a grip handle and a movable handle.

In this process, the grip handle is securely gripped in the palm of the operator's hand and the thumb is on the movable handle. By moving the thumb, the operator activates the handle in such a way that the electrode can be moved along the longitudinal axis into working position or into the housing.

Through spring tension the electrode can be automatically retracted into the housing, so that injuries are avoided or any damage to the electrode is prevented. The electrode can be exposed or covered up alternatively or in combination, by means of longitudinal sliding of the housing which is connected to the handle.

BRIEF DESCRIPTION OF THE DRAWINGS

The invention is elucidated by means of diagrams and various models.

Illustrations are as follows:

FIGS. 2a and 2b An additional model of the surgical instrument with exchangeable electrode FIGS. 3 and 4 Further models of the surgical instrument with elbowed housing FIGS. 5 and 6 Two models with movable electrode mounting FIGS. 7a and 7b A model with slidable housing or protective sleeve.

SPECIFIC DESCRIPTION

Figure 1:
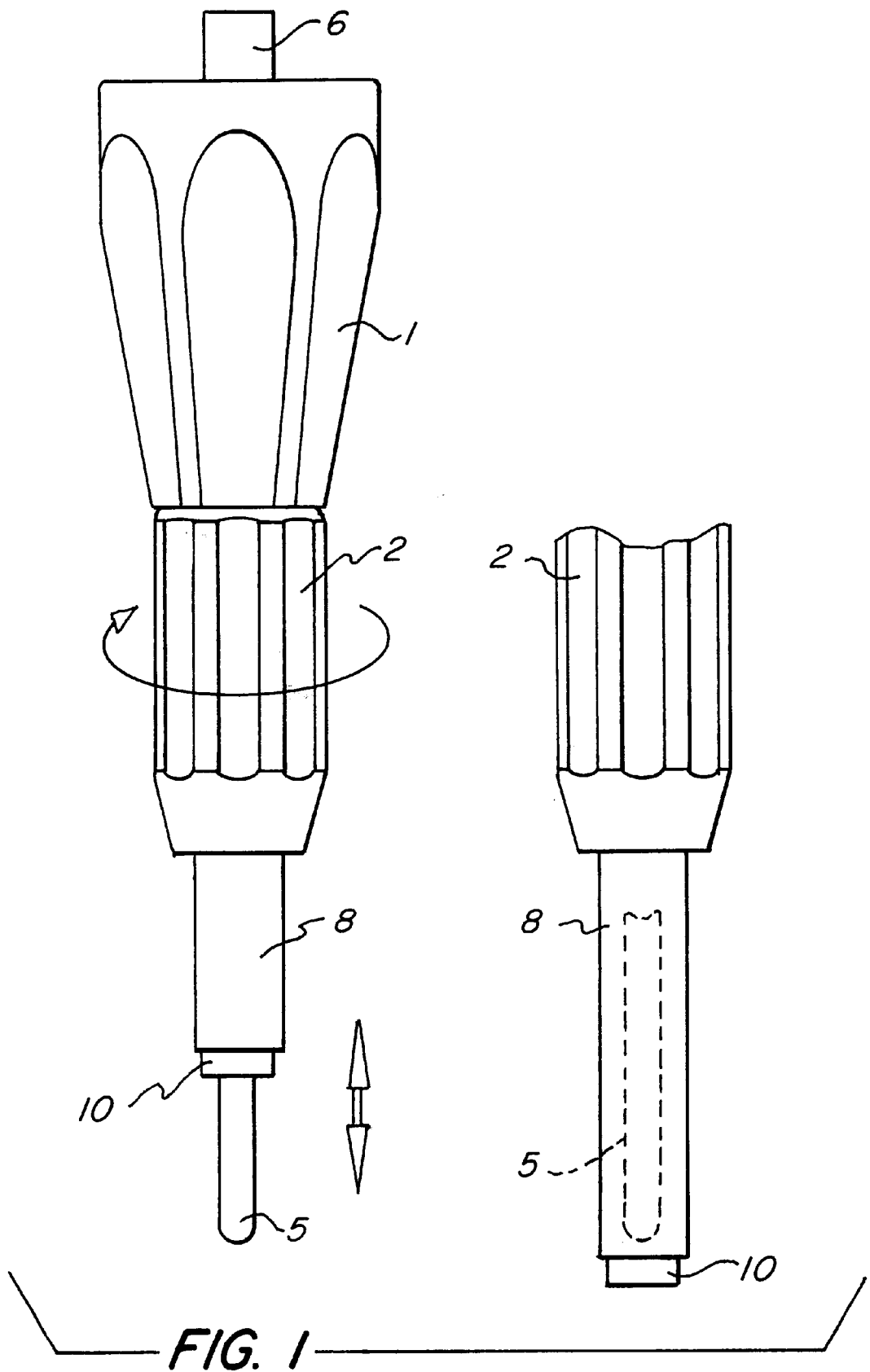
FIG. 1 An initial model of the surgical instrument
Figure 3:
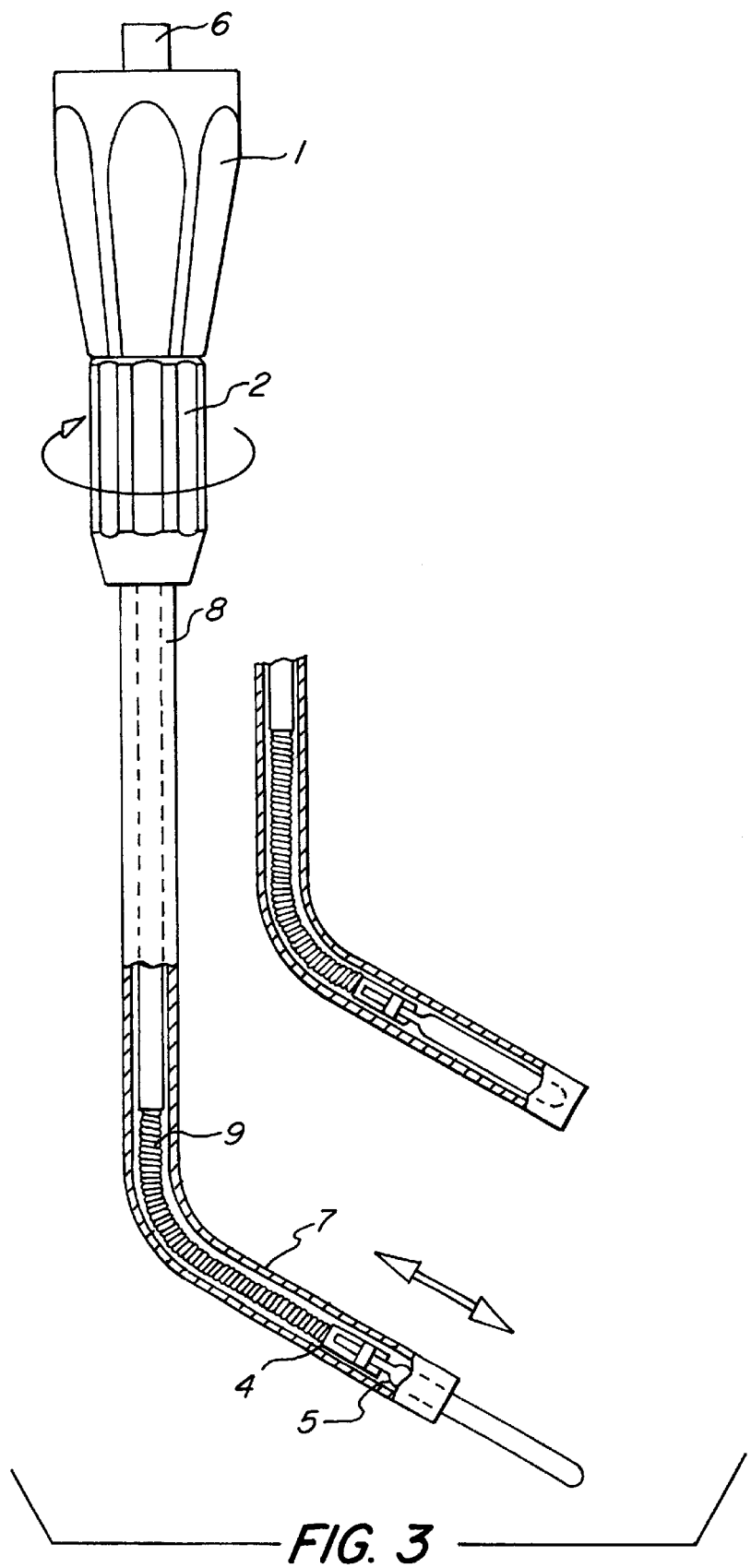
Figure 4:
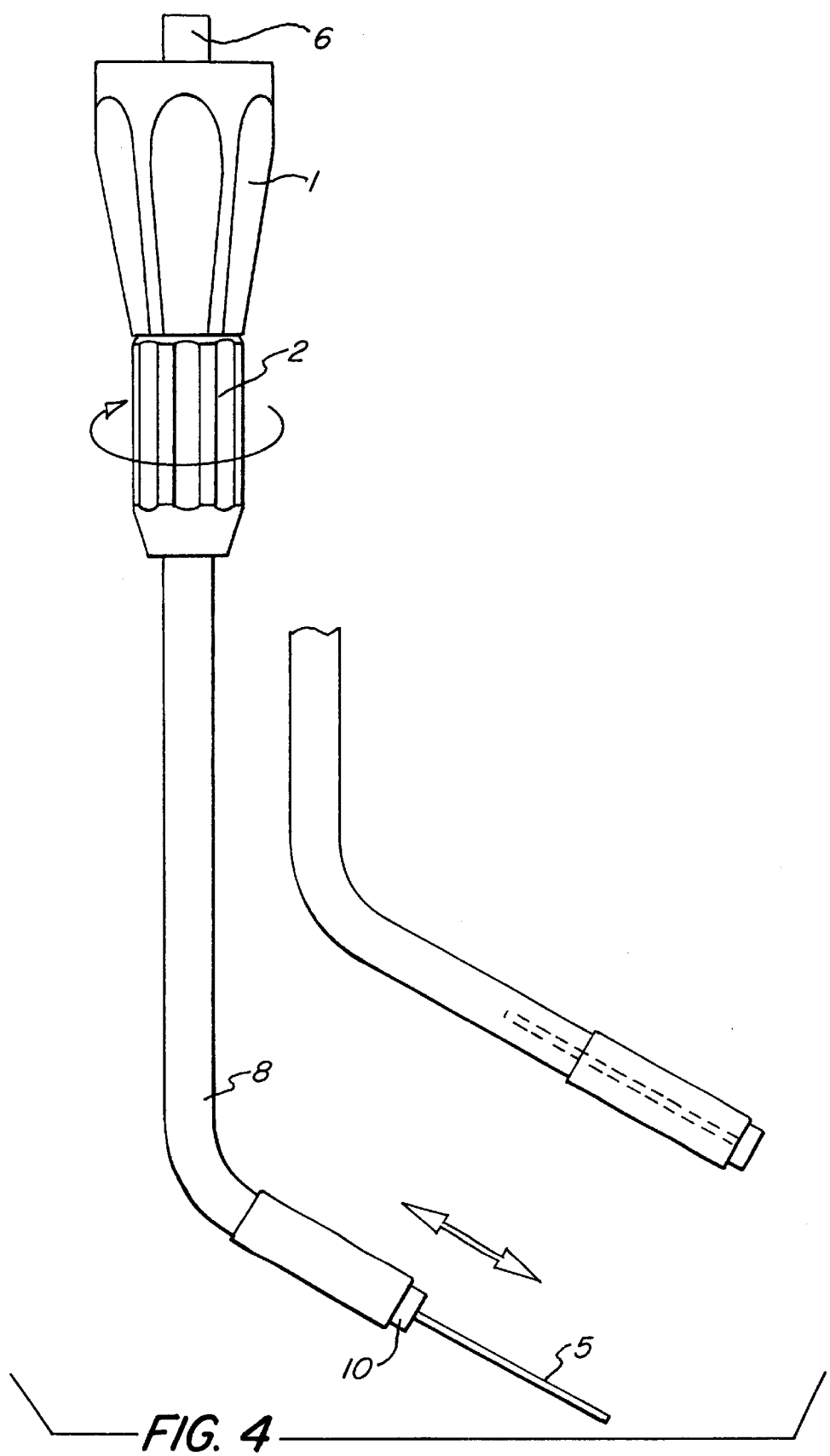

The surgical instrument as shown in FIGS. 1, 2a, and 2b includes an electrode 5 (in various models, for instance as a needle in FIG. 4, or as a spatula in FIGS. 2 and 3) secured with a catch or clamp device 4 or the like on an electrode mounting 11, a housing 8 surrounding the electrode 5 and mounting 11, with an outer thread 3 at the handle grip end, as well as a handling device with gas and high-frequency electrical supply, connected with mounting 8 and electrode mounting 11.

The handling device consists of a longitudinal arrangement of a grip handle 1 with the gas and high-voltage current supply 6 and can be installed into a gripping device (not shown). A turn handle 2 is joined to the grip handle 1 at the distal end with an inside thread 2a, which corresponds with the outer thread 3 of the housing 8 and engages with it.

The electrode mounting 11 is secured in grip handle 1.

During use, the surgical instrument is held with the grip handle 1 and the gripping device in the palm of the operator's hand, so that the operator can move the turn handle 2 with the thumb. The thread 2a, 3 is designed in such a way that approximately with one quarter-turn of the turn handle 2, the electrode 5 is freed for cutting, by means of the housing 8 being moved from the electrode. With a contrariwise thumb motion, housing 8 is again moved over the electrode 5, and the electrode is again protected. Simultaneously with the electrode motion the instrument's operating mode can be activated or changed.

In a more developed model of the instrument, the turn handle 2 is equipped with a spring power in such a way the when the electrode is freed, the spring is tensed. If a catch button or the turn handle is again released, then the housing moves again on its own over the electrode.

A third model, then, includes a locking element on turn handle 2 in the form of the catch button or similar item (not shown), by means of which through thumb pressure the tensed spring can be stopped and again released.

A fourth model concerns the formation of the handle end of the electrode mounting 11 as a spindle or the like. The inside thread 2a of the turn handle 2 engages with the thread 11a of the electrode mounting, so that the electrode 5 can be moved into or out of the housing 8.

A fifth version features a bendable housing 8 (FIGS. 3 and 4) on the distal end, making it easier to reach operation fields that are difficult to gain access to. For this purpose the elecrode mounting 11 is flexible, preferably made of a bendable spiral 9.

Figure 5:
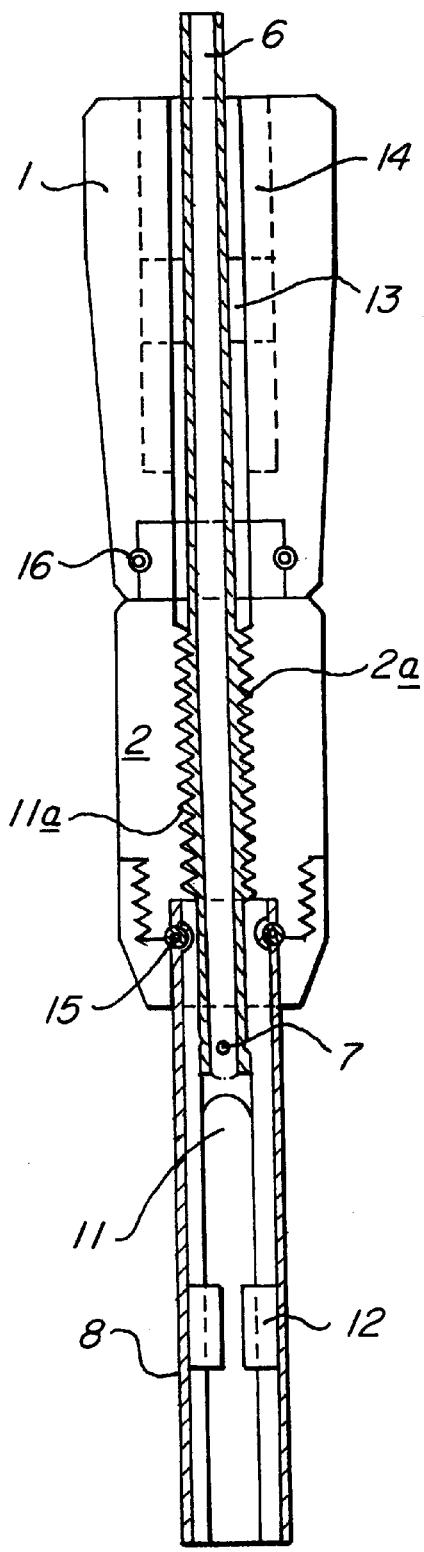

FIG. 5 shows a sixth execution model in which the electrode mounting 11 is equipped on the handle side with an outer thread 11a, which engages with the inside thread 2a of the turn handle 2. To control the electrode mounting 11, this mounting on the handle side is equipped with at least two radially distanced wings 13, which move in a corresponding guide groove 14 along the longitudinal axis in the grip handle 1.

On the distal end, the otherwise pipe-like electrode mounting 11 is flattened in form, and moves longitudinally in two pairs of guide rails 12, which are arranged in the housing 8. In order to ensure turnability of the turn handle 2 with respect to housing 8 on the one hand, and with respect to grip handle 1 on the other hand, on the relevant spots there are bearings installed, preferably ball bearings or slide bearings 15, 16. An inert gas such as argon is introduced at the grip handle end of the electrode mounting 11, which end extends out of the grip handle 1 as supports 6, and this gas then streams through the bore holes 7 into the housing and from there surrounds the electrode 5 and the corresponding operating field.

Figure 6:
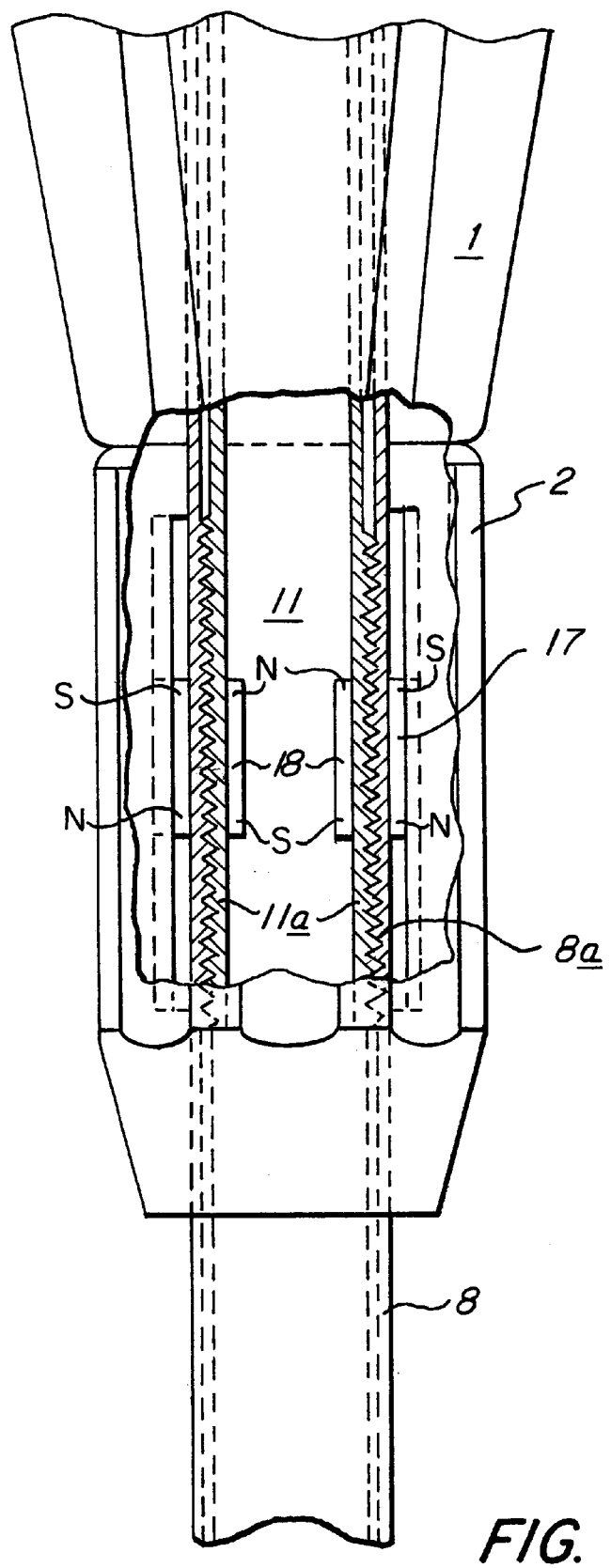

A seventh model, as shown in FIG. 6, includes the movement of the electrode by means of a magnetomechanical device installed in the turn handle 2. For this purpose, a cylindrical undercutting is made longitudinally in the turn handle 2, containing at least two permanent magnetic strips 17 that can move longitudinally. These magnetic strips are guided in radial guide grooves.

In the housing 8, which is secured in the grip handle 1, in the area of the turn handle 2 there is an inside thread 8a formed which engages with an outer thread 11a on the pipe-like electrode mounting 11.

Additional magnets 18 are secured in the electrode mounting 11 opposite the movable magnets 17. If turn handle 2 is turned with the magnets 17, the effect of the magnetic fields also draws the magnets 18 in the electrode mounting 11. Because of threads 8a, 11a, through the rotation motion the electrode mounting 11 moves in the longitudinal direction. Instead of magnetic strips it is possible to use circular ring shaped or circle-segment shaped magnets.

In the seventh model, as shown in FIGS. 7a and 7b, there is a longitudinally slidable housing in the form of a protective sleeve 20. The sleeve has a grip trough or a grip ring 21. Along an extension 23, the grip ring 21 and thus the protective sleeve 20 are held movably in a guide boring of the grip handle 1. A surrounding collar 24, in connection with a shoulder 25 inside the grip handle 1, sets up a limit to the longitudinal sliding course of the protective sleeve 20, so that the electrode 22 can be covered and uncovered without any danger of the undesired complete withdrawal of the protective sleeve 20. This occurs through the sliding of the protective sleeve 20 by means of an effective force in the area of grip ring 21. To maintain the movable catch positions of the protective sleeve 20, the extension 23 has catch recesses 26, for instance in the form of a surrounding groove. Spring-laden catch pins or catch spheres 27 then engage with this groove. Of course, a kinematic reversal of the sequence of catch recesses and catch pins or catch spheres is also possible.

The proposed surgical instrument is easily produced, simple and safe in handling. The safeguarding of the cutting or coagulation elecrode through a possible retraction into the housing, on the one hand, protects the electrode, and on the other, avoids possible danger of injury.

What is claimed is:

1. Surgical instrument, including an operating device, a gas and high-voltage current supply, a housing, as well as an electrode which is installed on an electrode mounting in the housing, the instrument distinguished by the fact that the operating device consists of a longitudinal arrangement of a grip handle, a turntable turn handle connected at the distal end, against the grip handle with an inside thread;

the housing is equipped on the grip side with an outer thread corresponding to the inside thread of the turn handle which outer thread engages with the inside thread so that, through a turning of the turn handle, the housing can be moved longitudinally forward or backward; and that the electrode in the housing is secured to a holding element, which is connected with the grip handle on the grip side.

2. Surgical instrument according to claim 1, distinguished by the fact that the electrode mounting (11) is shaped on the grip side like a spindle or similar object, whose thread (11a) instead of the outer thread (3) of the housing (8) is engaged with the inside thread (2a) of the turn handle (2) and thus the electrode (5) is movable longitudinally in the housing (8).

3. Surgical instrument according to claim 2, distinguished by the fact that the thread (11a) of the electrode mounting (11) engages with the inside thread (8a) of the housing (8) and that the turning motion of the turn handle (2) by means of magnets (17, 18) in the turn handle (2) and in the electrode mounting (11) is transmitted to the electrode mounting (11) and the electrode mounting is moved longitudinally over the thread arrangement (8a, 11a) in the housing (8).

4. Surgical instrument according to claim 1, distinguished by the fact that the thread pitch of the inside thread (2a or 8a) and outer thread (3) or of the spindle thread (11a) is arranged in such a way that the electrode (5) can be freed or covered with basically just a quarter-turn of the turn handle (2).

5. Surgical instrument according to claim 1, distinguished by the fact that the turn handle (2) is equipped with a spring in such a way that upon release of the electrode (5) the spring is tensed, so that when the turn handle (2) is freed, the electrode is independently covered up again.

6. Surgical instrument according to claim 1, distinguished by the fact that for stopping the spring on the turn handle (2) a securing element is installed, which unlocks the spring, for instance through thumb pressure.

7. Surgical instrument according to claim 1, distinguished by the fact that the housing (8) is bent at an angle or is flexible.

8. Surgical instrument according to claim 7, distinguished by the fact that the distal end of the electrode mounting (11) is flexible, preferably in the form of a spiral spring (9).

9. Surgical instrument according to claim 1, distinguished by the fact that the electrode mounting (11) is designed in such a way that the electrodes (5) are replaceable.

10. Surgical instrument, including an operating device, a gas and high-voltage current supply, a housing, an electrode which is installed on an electrode mounting in the housing the instrument distinguished by the fact that the operating device consists of a longitudinal arrangement of a grip handle and a distally connected handle movable in relation to the grip handle, with a grip ring;

the housing is connected with a grip ring or handle, so that through a longitudinal sliding of the handle, the housing can be moved longitudinally forward or backward to expose or cover up the electrode, and that in the housing the electrode is secured to a holding element which is connected with the grip handle.

11. Surgical instrument according to claim 10, distinguished by the fact that the grip handle (1) has a guide bore to receive an extension (23), which is connected with the grip ring (21) and/or the housing (20) which forms a protective sleeve.

12. Surgical instrument according to claim 11, distinguished by the fact that inside the guide bore a shoulder (25) is formed, which together with a surrounding coil (24) of the extension (23) forms a slide prevention or slide limitation device.

13. Surgical instrument according to claim 11, distinguished by the fact that in order to hold the movable catch positions of the protective sleeve, the extension (23) has catch recesses (26), which interact with catch pins or catch spheres (27) of the grip handle.

14. A surgical instrument for high-frequency surgery, comprising:

a gas supply line for argon-plasma coagulation a grip handle extending along a longitudinal axis and having a distal end;

an electrode spaced axially from the grip handle and connected thereto;

a turn handle between the grip handle and the electrode coaxial with the grip handle and rotatable about the longitudinal axis relative to the grip handle and the electrode, said turn handle having an inner thread; and a housing having one of its opposite ends surrounding the electrode and the other end provided with an outer thread which meshes with the inner thread of the turn handle to provide axial displacement of the housing relative to the electrode upon actuating of the turn handle.

* * * * *